United States Patent
Karl et al.

(10) Patent No.: US 11,458,020 B2
(45) Date of Patent: Oct. 4, 2022

(54) METHOD AND DEVICE FOR PRODUCING AN IMPLANT

(71) Applicant: Christoph Karl, Kreuzlingen (CH)

(72) Inventors: Christoph Karl, Kreuzlingen (CH); Zully Ritter, Werder (DE)

(73) Assignee: Christoph Karl, Kreuzlingen (CH)

( * ) Notice: Subject to any disclaimer, the term of this patent is extended or adjusted under 35 U.S.C. 154(b) by 60 days.

(21) Appl. No.: 17/059,718

(22) PCT Filed: Mar. 12, 2019

(86) PCT No.: PCT/EP2019/056123
§ 371 (c)(1),
(2) Date: Nov. 30, 2020

(87) PCT Pub. No.: WO2019/233641
PCT Pub. Date: Dec. 12, 2019

(65) Prior Publication Data
US 2021/0212834 A1    Jul. 15, 2021

(30) Foreign Application Priority Data
Jun. 7, 2018 (DE) .................... 10 2018 113 580.7

(51) Int. Cl.
*A61F 2/30* (2006.01)
*B33Y 10/00* (2015.01)
(Continued)

(52) U.S. Cl.
CPC ...... *A61F 2/30942* (2013.01); *A61F 2/30771* (2013.01); *A61F 2/3609* (2013.01);
(Continued)

(58) Field of Classification Search
CPC ..... A61F 2/30942; B33Y 10/00; B33Y 50/00; B33Y 50/02
See application file for complete search history.

(56) References Cited

U.S. PATENT DOCUMENTS 3,707,006 A * 12/1972 Bokros ............... A61F 2/30965
                                                    433/201.1
5,364,400 A * 11/1994 Rego, Jr. ................ A61L 31/10
                                                    606/77
(Continued)

FOREIGN PATENT DOCUMENTS

CN    107714078    2/2018
DE    69432023    10/2003
(Continued)

OTHER PUBLICATIONS

Fuller et al. "High resolution peripheral quantitative computed tomography for the assessment of morphological and mechanical bone parameters." Revista Brasileira de Reumatologia (English Edition) vol. 55, Issue 4, Jul.-Aug. 2015, pp. 352-362 (Year: 2015).*

*Primary Examiner* — Cachet I Proctor
(74) *Attorney, Agent, or Firm* — Duane Morris LLP; Gregory M. Lefkowitz; Randall C. Pyles

(57) ABSTRACT

The invention relates to a method and a device for producing an implant, wherein a natural bone microstructure of a natural bone region is detected (S1), an implant region in the natural bone region is marked (S2), the detected bone microstructure in the marked implant region is analysed to determine reproduction parameters (S3), and on the basis of the determined reproduction parameters, an artificial microstructure for producing the implant is created (S4).

19 Claims, 11 Drawing Sheets

(51) Int. Cl.
*B33Y 50/00* (2015.01)
*B33Y 30/00* (2015.01)
*B33Y 80/00* (2015.01)
*A61F 2/36* (2006.01)
*A61F 2/38* (2006.01)
*A61F 2/42* (2006.01)
*A61L 27/04* (2006.01)
*A61L 27/06* (2006.01)
*A61L 27/10* (2006.01)
*A61L 27/12* (2006.01)
*A61L 27/16* (2006.01)
*A61L 27/18* (2006.01)
*A61L 27/26* (2006.01)
*A61L 27/54* (2006.01)

(52) U.S. Cl.
CPC .......... *A61F 2/3877* (2013.01); *A61F 2/4202* (2013.01); *A61F 2/4225* (2013.01); *A61F 2/4241* (2013.01); *A61L 27/042* (2013.01); *A61L 27/045* (2013.01); *A61L 27/047* (2013.01); *A61L 27/06* (2013.01); *A61L 27/10* (2013.01); *A61L 27/105* (2013.01); *A61L 27/12* (2013.01); *A61L 27/16* (2013.01); *A61L 27/18* (2013.01); *A61L 27/26* (2013.01); *A61L 27/54* (2013.01); *B33Y 10/00* (2014.12); *B33Y 30/00* (2014.12); *B33Y 50/00* (2014.12); *B33Y 80/00* (2014.12); *A61F 2002/3006* (2013.01); *A61F 2002/3093* (2013.01); *A61F 2002/30784* (2013.01); *A61F 2002/30948* (2013.01); *A61F 2002/30952* (2013.01); *A61F 2002/30985* (2013.01); *A61F 2310/00017* (2013.01); *A61F 2310/00023* (2013.01); *A61F 2310/00029* (2013.01); *A61F 2310/00041* (2013.01); *A61F 2310/00203* (2013.01); *A61F 2310/00215* (2013.01); *A61F 2310/00239* (2013.01); *A61F 2310/00293* (2013.01); *A61L 2300/414* (2013.01); *A61L 2420/02* (2013.01); *A61L 2430/24* (2013.01)

(56) References Cited

U.S. PATENT DOCUMENTS

| | | | | |
|---|---|---|---|---|
| 5,658,288 A | * | 8/1997 | Kim | A61B 17/7225 606/316 |
| 5,759,190 A | * | 6/1998 | Vibe-Hansen | A61F 2/30756 602/41 |
| 6,458,119 B1 | * | 10/2002 | Berenstein | A61B 17/12163 606/1 |
| 7,468,075 B2 | * | 12/2008 | Lang | A61F 2/30942 606/88 |
| 7,796,791 B2 | * | 9/2010 | Tsougarakis | G06T 7/0012 382/128 |
| 7,799,077 B2 | * | 9/2010 | Lang | A61F 2/4261 606/86 R |
| 7,842,054 B2 | * | 11/2010 | Greene, Jr. | A61B 17/12118 604/93.01 |
| 8,337,507 B2 | * | 12/2012 | Lang | G06F 30/00 606/86 R |
| 8,556,983 B2 | * | 10/2013 | Bojarski | A61F 2/30942 606/86 R |
| 9,020,788 B2 | * | 4/2015 | Lang | A61F 2/3859 703/6 |
| 9,603,711 B2 | * | 3/2017 | Bojarski | A61B 17/155 |
| 9,763,683 B2 | | 9/2017 | Bonutti | |
| 10,064,726 B1 | * | 9/2018 | Wei | B29C 64/386 |
| 2002/0091396 A1 | * | 7/2002 | Vibe-Hansen | A61F 2/2846 606/151 |
| 2004/0138754 A1 | * | 7/2004 | Lang | A61F 2/30756 623/20.14 |
| 2006/0204738 A1 | * | 9/2006 | Dubrow | A61F 13/02 428/292.1 |
| 2008/0195211 A1 | * | 8/2008 | Lin | A61P 19/08 382/128 |
| 2009/0187259 A1 | | 7/2009 | Argenta | |
| 2009/0270868 A1 | | 10/2009 | Park | |
| 2011/0276159 A1 | * | 11/2011 | Chun | A61C 13/0004 700/98 |
| 2014/0099017 A1 | * | 4/2014 | Tsai | G06T 7/596 382/154 |
| 2017/0181798 A1 | | 6/2017 | Panescu | |
| 2017/0232142 A1 | * | 8/2017 | Santerre | C08F 283/008 514/772.6 |
| 2018/0055643 A1 | * | 3/2018 | Castro | B33Y 80/00 |

FOREIGN PATENT DOCUMENTS

| | | |
|---|---|---|
| EP | 1450875 | 9/2004 |
| EP | 3266418 | 1/2018 |
| TW | I554251 | 10/2016 |
| WO | 2015/185219 | 12/2015 |
| WO | WO-2015185219 A1 * 12/2015 | ............ A61B 17/16 |

* cited by examiner

Here, dodecanediol as a rel. nonpolar "chain extender": reaction with prepolymers

IB

IB   nKM₁

3D-mKM

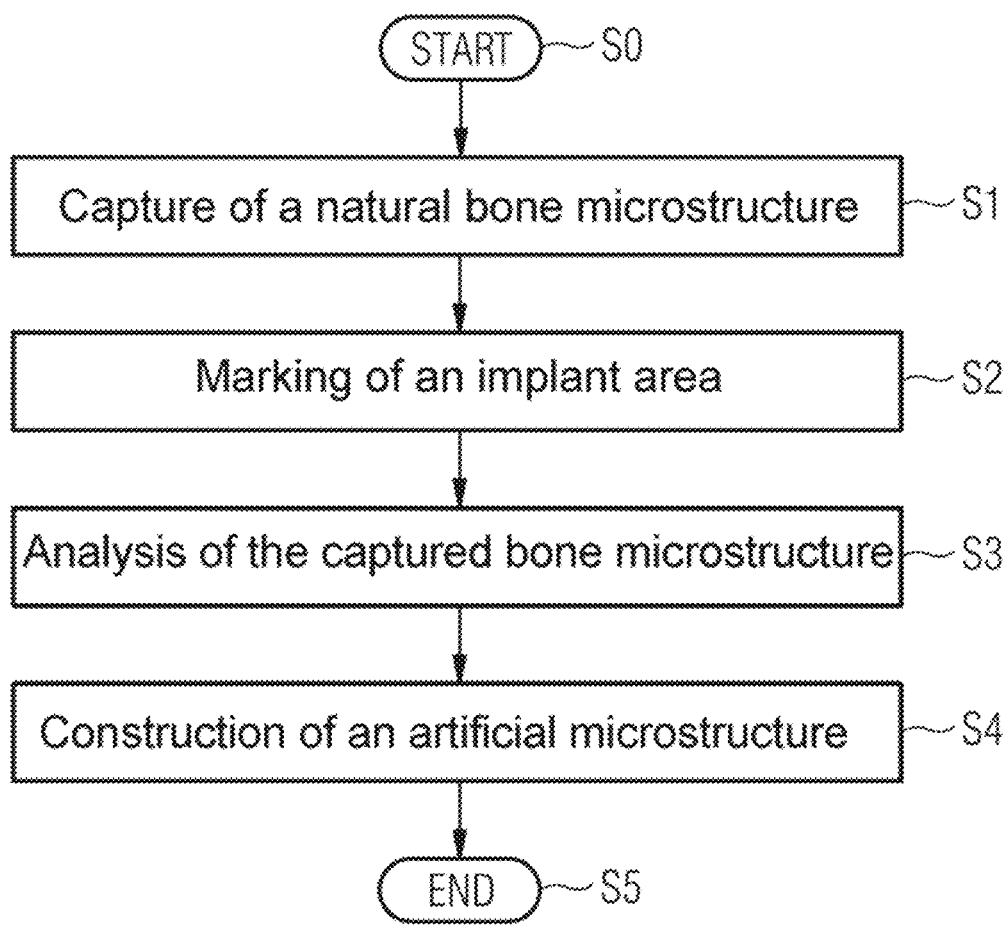

METHOD AND DEVICE FOR PRODUCING AN IMPLANT

CROSS-REFERENCE TO RELATED APPLICATIONS

This application is a § 371 national stage entry of International Application No. PCT/EP2019/056123, filed on Mar. 12, 2019, which claims priority to German Patent Application No. 10 2018 113 580.7, filed on Jun. 7, 2018, the entire contents of which are incorporated herein by reference.

The present invention relates to a method and a device for producing an implant and in particular to a method and a device for producing a joint implant for new tissue formation at the joint such as, e.g., a joint implant for new cartilage formation at the knee, hip, shoulder, ankle, metatarsophalangeal or hand joint.

Joint diseases (arthrosis) are among the ten most common disease types worldwide. Arthrosis is painful, and without treatment, it can lead to immobility of the affected joints and even to total joint replacement. Total replacement of the affected joint is quite costly and ordinarily places a psychological burden on the patient. Revisions of the joint replacement involve further costs, stress for the patient, and often complications. Various approaches have therefore been developed for the curative treatment of joint diseases (arthrosis) and in particular for the curative treatment of knee and hip joint arthrosis in order to avoid joint replacement.

The approaches currently available for the curative treatment of joint diseases are explained below.

Drug treatment options: Drug treatment options are limited to the symptomatic use of anti-inflammatories and analgesics and sometimes intra-articular, sometimes systemic treatment with hyaluronic acid, chondroitin sulphate, interleukin-1 receptor antagonists and glucosamine sulphate. Although such treatment has shown good results in pain reduction, it has not yet been successful in preventing the progression of arthrosis.

Surgical therapies: surgical therapies as well such as local bone or cartilage transplantation or autologous chondrocyte transplantation or implantation (ACT or ACI) have not yet become established, because such therapies require two operations (removal and re-implantation), which means that the joint bears no load or is immobilized during rehabilitation and which thus adversely affects regeneration. Moreover, the still-healthy cartilage at the removal site is also damaged.

The most widespread therapies are therefore surgical therapies such as so-called Pridie drilling, anterograde/retrograde drilling and microfracturing. In these surgical therapies, the local cartilage is not replaced; rather, for example, multiple perforations are carried out through the subchondral border lamella. In Pridie drilling and microfracturing, which is a further development thereof, bleeding into the cartilage defect can be achieved in the defect area, allowing fibrocytes, mesenchymal stem cells and chondroblasts from the cancellous space to wash into the cartilage defect. These combine with growth factors to form a blood clot ("super clot") and differentiate into articular cartilage. Clinical studies have shown reduction of pain and favourable joint mobility. However, the long-term removal of weight or immobilization of the joint is a problem in this case as well, leading as a rule to the development of poor-quality regenerative fibrous cartilage. Due to its structure, this cartilage is often insufficient to support the high mechanical loads placed on the knee joint in particular and degenerates rapidly, which can necessitate further surgical interventions.

For this reason, carbon rods have been developed as joint implants for new tissue formation at the joint that are placed in the bore holes and are designed to be rapidly overgrown.

EP 1450875 A1 discloses such a joint implant for new tissue formation at the joint, wherein the rods used are composed of densified carbon with a predetermined porosity. The use of such conventional carbon rods also allows fibrocytes and mesenchymal stem cells to be washed from the cancellous space into the cartilage defect, forming a "super clot" and differentiating into articular cartilage.

Because of two significant drawbacks, however, this system has not yet become established. On the one hand, carbon is not accepted by orthopaedic surgeons as an active component for use in cartilage because of the risk of microabrasion. On the other hand, the surface is not designed for colonisation by stem cells, which also manifests itself in the development of poor-quality regenerative fibrous cartilage.

Because of these limitations, none of the above-mentioned therapies have yet become established as a standard of care.

The object of the invention is therefore to provide a method and a device for producing an implant that provides improved properties in new tissue formation.

According to the invention, this object is achieved in respect of the method by means of the features of claim 1 and in respect of the device by means of the features of claim 11.

Especially by capturing a natural bone microstructure of a natural bone area, marking an implant area in the natural bone area, analysing the captured bone microstructure in the marked implant area to ascertain reproduction parameters, and constructing an artificial microstructure on the basis of the ascertained reproduction parameters, it is possible to produce an implant having a microstructure very similar or identical to the bone area to be treated. As a result, it is possible to realize a natural transition between implant and still healthy bone area, resulting in promotion of natural healing on an individual basis.

For example, the natural bone microstructure is captured by a high-resolution peripheral quantitative computed tomography method (HR-pQCT), which provides a multiplicity of 2D sectional views of a bone area to be examined. As a result, a 3-dimensional (3D) image of the bone area to be examined can be generated with particularly high quality.

For example, a multiplicity of disc parameters or a multiplicity of trabecular parameters are ascertained as reproduction parameters when analysing the captured bone microstructure, the result being that the further processing of the data or the production of the implant is substantially simplified.

Preferably, constructing the artificial microstructure is realized by means of a 3D printing method, the result being that the production costs are further lowered while quality and precision are high.

For example, the artificial microstructure of the implant is an artificial stacked-disc structure or an artificial trabecular structure. As a result, the costs and the time requirement for production are further lowered.

Preferably, the implant is a rod-shaped joint implant for new tissue formation at a joint, having a hydrophobic surface to promote chondrocytic differentiation of mesenchymal stem cells. As a result, one can achieve an improvement in new tissue formation and in particular new cartilage formation at the joint and the formation of higher-quality weight-bearing cartilage. It is also possible to achieve cartilage regeneration that is long-lasting, and because of the continuous transport of mesenchymal stem cells in the direction of the joint space, sustainable, and this cartilage regeneration can either allow further surgery on the joint to be delayed or obviate the need for such surgery.

For example, the material used in the production of the implant is a polymer, in particular PA, PEK, PEKK, PEEK, UHMWPE or PCL, a metal, in particular Ti or stainless steel, a metal alloy, in particular Ti64 or CoCr, a magnesium alloy, in particular Mg—Ca, Mg—Zr or Mg—Zn, a ceramic, in particular $Al_2O_3$, $ZrO_2$ or $Ca_3(PO_4)_2$, or $Si_3N_4$ or in vivo resorbable Mg alloy, the result being that it is possible to realize a high-mechanical-strength implant having improved properties for new tissue formation for many different areas of use. Preferably, the artificial microstructure is coated with a hydrophobic chemical material, thus allowing chondrocyte differentiation to be implemented in a particularly simple and effective manner.

For example, a growth factor can be applied to the artificial microstructure to promote chondrocytic differentiation of mesenchymal stem cells, in particular FGF-1, FGF-2, FGF-10 to FGF-22, SDF-1, IGF-1, PDGF, TGF-$\beta$1 and TGF-$\beta$3, BMP-2 and BMP-7, OP-1, PRP or bioinert polyamide, thus further improving the differentiation of cartilage and the growth of tissue, and in particular of cartilage material on the joint implant and at the defect site.

The device for producing an implant preferably comprises a capture device for capturing a natural bone microstructure of a natural bone area, a marking device for marking an implant area in the natural bone area, an analysis device for analysing the captured bone microstructure in the marked implant area and for ascertaining reproduction parameters, and a reproduction device for constructing an artificial microstructure on the basis of the ascertained reproduction parameters and for producing the implant.

Preferably, there is provided at least one transmission device for sending/receiving the captured bone microstructure, the marked implant area and/or the ascertained reproduction parameters, thus allowing a particularly effective and cost-effective production of individual implants.

Further advantageous embodiments of the invention are characterized in the further dependent claims.

The invention is described in further detail below using examples with reference to the drawing.

The figures show the following:

FIG. 13 shows a simplified flow chart of a method for producing an implant according to a further example of the invention.

Figure 1:
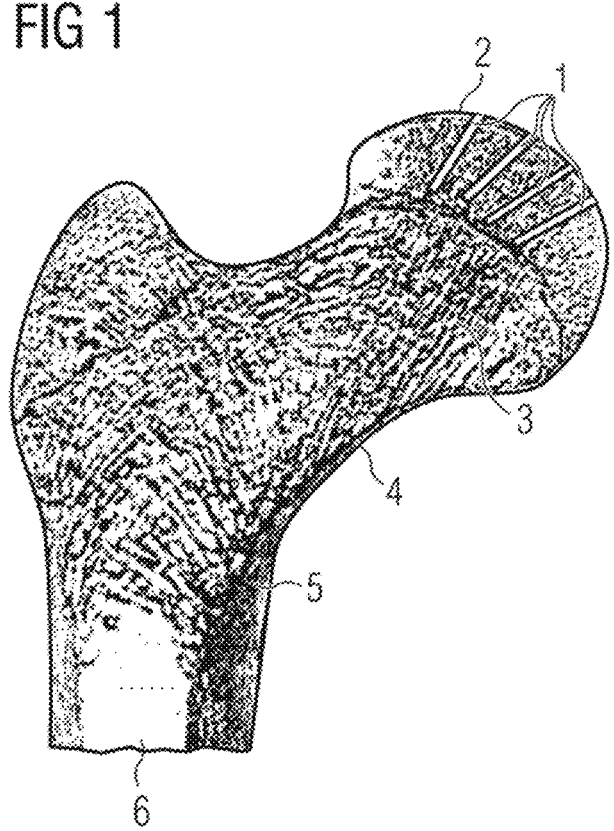
FIG. 1 is a simplified sectional view of a femoral bone with implants according to the invention.

FIG. 1 shows a simplified sectional view of an upper section of a femoral bone as an example illustrating the use of the implants or joint implants according to the invention for new tissue formation at a femoral/hip joint. In FIG. 1, reference number 1 denotes the implants or joint implants according to the invention, which can be inserted in the area of the implants or joint into the femoral bone. In this process, for example in damaged cartilage areas 2, one or a plurality of indentations can be drilled, stamped, or otherwise formed in the bone, after which a respective joint implant 1 can be inserted in the respectively formed indentation. The respective indentation is preferably dimensioned such that the joint implant 1 used or the cover area thereof does not protrude at the surface of the bone or cartilage 2, but is flush therewith, or the cover area of the joint implant 1 is preferably below the surface of the bone or cartilage 2. The articular cartilage 2 damaged because of joint disease (arthrosis) can be at least partially regenerated by means of the joint implants according to the invention 1, as new formation of tissue, and in particular of articular cartilage, takes place at the ends or in the cover areas of the inserted joint implants 1.

According to FIG. 1, the bone comprises a periosteum 4 covering the bone, wherein a natural bone microstructure or natural trabecular structure is present at the end areas 3 of the bone that is referred to as the so-called spongiosa. Furthermore, in its middle area, the bone comprises relatively solid cortical bone 5 and in its interior a medullary cavity 6.

By using an implant 1 having an artificial microstructure or an artificial trabecular structure that is identical or very similar to the natural bone microstructure, it is possible to achieve improved properties in the regeneration and/or prevention of weakened bone areas or tissues, and this will be explained in detail below.

Figure 2A:
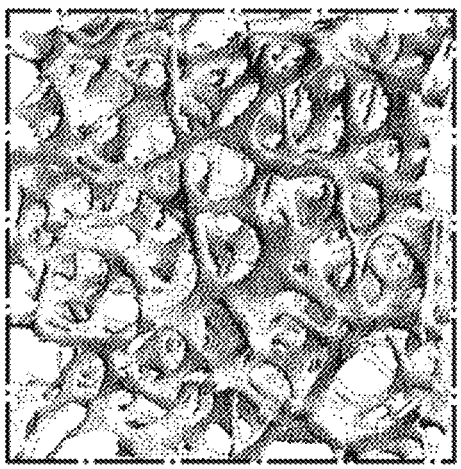
FIGS. 2A and 2B are simplified perspective views of natural bone microstructures (trabecular structures)
Figure 2B:
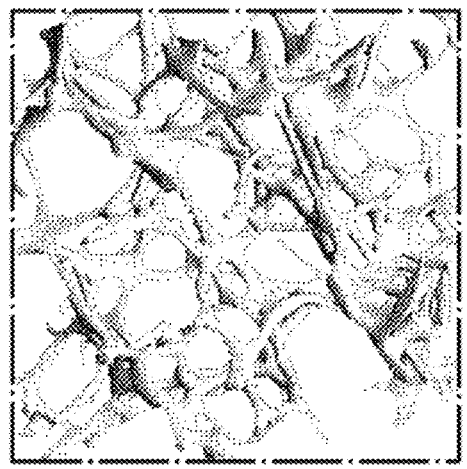

FIGS. 2A and 2B show simplified perspective views of natural bone microstructures or trabecular structures, such as those present for example in the cancellous bone area 3 of the human femoral bone. As shown in FIG. 2A, the cancellous bone area 3 of a young, healthy person is permeated with a highly fine and dense natural bone microstructure or trabecular structure, while as shown in FIG. 2B, an older person, in particular suffering e.g. from osteoporosis, often shows a sharply altered natural bone microstructure or trabecular structure with only a few, very thin trabeculae in the cancellous bone area 3.

For example, as joint implant 1, the implant can comprise a rod-shaped body that has an artificial microstructure or trabecular structure which is similar or identical to the bone area to be replaced. The artificial microstructure or trabecular structure, which is at least partly open or permeable to fluids, of the implant 1 which substantially corresponds to the natural bone microstructure of the bone area to be replaced allows for example rapid colonisation of the trabecular surface and in particular the part of the rod-shaped implant pointing towards the cartilage area with cartilage-forming cells such as e.g. chondroblasts, which results in significantly accelerated and at the same time long-lasting overgrowth and further allows the formation of high-quality regenerative cartilage.

FIGS. 3A to 3F show simplified perspective views of artificial trabecular structures. The artificial trabecular structure comprises a plurality of rod-shaped or plate-shaped elements (trabeculae), which when connected to one another give rise to a 3-dimensional microarchitecture.

The artificial trabeculae, which are preferably produced by 3D printing technology and biomimetic, may not show values below or above certain parameters.

In the following, the essential reproduction parameters of the artificial microstructure or trabecular structure according to the invention are defined in further detail.

Figure 3A:
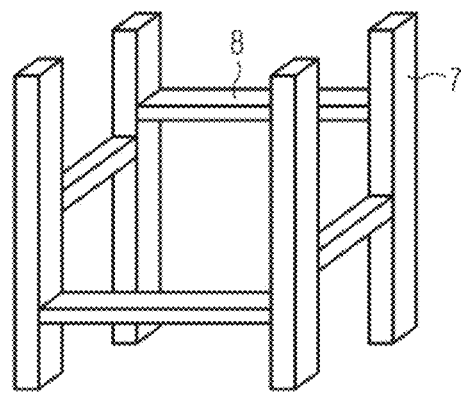
FIGS. 3A to 3F are simplified perspective views of artificial trabecular structures.
Figure 3B:
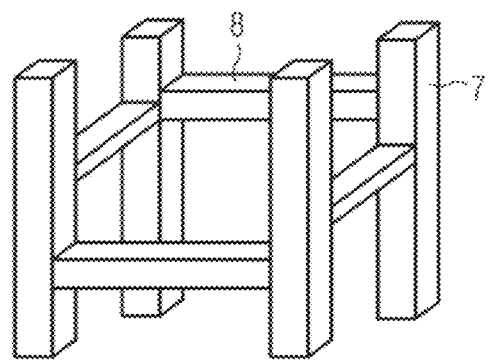

The so-called mean trabecular thickness (Tb.Th) defines the average trabecular thickness of the respective trabeculae or rod-shaped elements. For example, as the respective trabeculae according to FIG. 3A can have different forms, Tb.Th constitutes the average of the local thicknesses of all of the artificial trabeculae. The local thickness is derived e.g. in rectangular trabeculae from the trabecular diagonal and in circular trabeculae from the trabecular diameter. FIG. 3B shows a schematic diagram of the effects on the artificial microstructure of an increase in the average trabecular thickness Tb.Th. Preferably, the average trabecular thickness Tb.Th for the artificial trabecular structure is in the range of 100 to 500 μm, and in particular 150 to 400 μm.

Figure 3C:
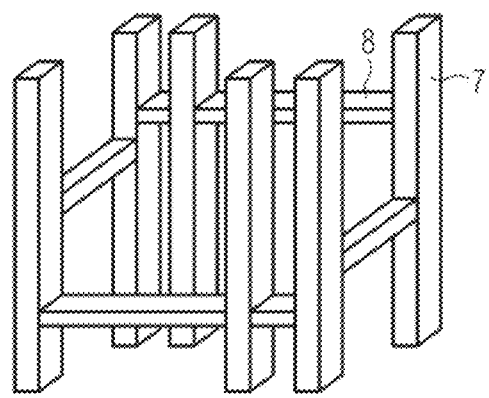
Figure 3D:
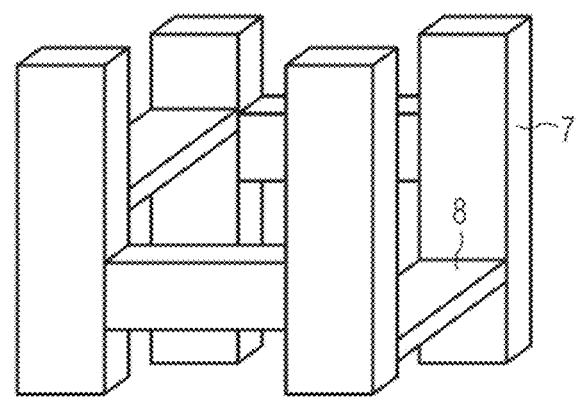

The so-called mean trabecular separation (Tb.Sp) defines the average trabecular separation analogously to the average trabecular thickness Tb.Th. A decrease in Tb.Sp can result from a change in various other parameters, e.g. an increase in Tb.Th (FIG. 3B), a decrease in Tb.N (FIG. 3C) or an increase in the structure model index (SMI) (FIG. 3D). The unit of average trabecular separation Tb.Sp is the μm and for the artificial trabecular structure of the present invention is preferably in a range of 100 μm to 900 μm, and in particular 200 μm to 600 μm.

The so-called trabecular number (Tb.N) is defined as the inverse function of the average distance between the axes of the plates and/or rods and indicates the number of trabeculae per mm. FIG. 3C shows for example an increase in Tb.N compared to FIG. 3A. Preferably, the trabecular number Tb.N of the artificial trabecular structure is in a range of 1 to 6 per mm, in particular in a range of 1.6 to 5.2 per mm.

The so-called "structure model index" (SMI) is a further descriptive parameter of the artificial trabecular structure, which for example can be a network composed of plate-like and rod-like elements. In fact, however, the trabecular network is not of one form or the other; rather, there is a fluid transition between them. With increasing age, for example, a more plate-like network is converted to a more rod-like one. Based on this realization, the so called structure model index (SMI) was introduced, which makes it possible to quantify the structure with respect to the number of plates and rods. For an ideal plate model, the SMI has a value of 0 (i.e. a pure plate structure), and for an ideal rod model, the value is 3. The SMI thus describes the relative composition of the artificial trabecular structure of plates and rods. FIG. 3D schematically shows a decrease in SMI. The SMI is dimensionless and for the present invention is for example 0.2 to 2.0, and preferably 0.25 to 1.8.

Figure 3E:
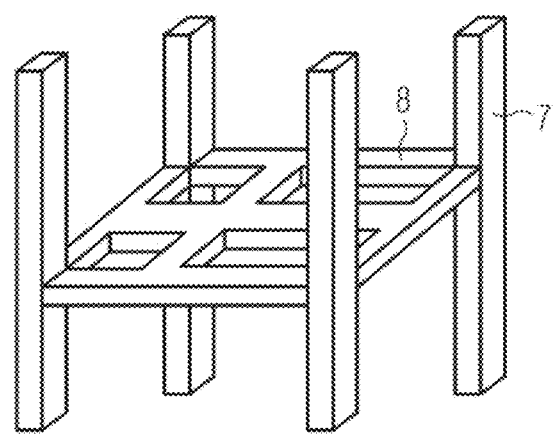

So-called connectivity-density (Conn.D) is a measure of the connectivity of the trabecular network. Connectivity is the maximum number of connections that can be disrupted within the network, e.g. by microfractures, without separating the network as a whole into two parts that are no longer connected to each other. FIG. 3E is a schematic diagram of an increase in connectivity-density Conn.D. Preferably, the connectivity density Conn.D of the artificial trabecular structure of the present invention is in a range of $1/mm^3$ to $60/mm^3$, in particular $1.5/mm^3$ to $45/mm^3$.

Figure 3F:
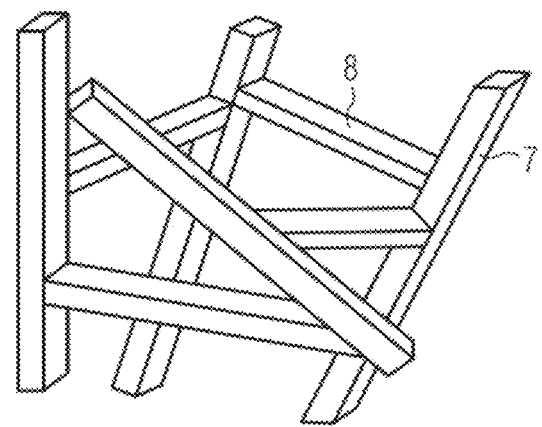

The geometric degree of anisotropy (DA) is a parameter for quantifying spatial asymmetry. The higher the DA, the greater the orientation of the artificial trabecular structure in a specified direction. FIG. 3F shows a schematic diagram of a decrease in DA. Like the parameter SMI, DA is also dimensionless. A DA of 0 indicates a perfectly isotropic structure, and a DA of 1 a perfectly anisotropic structure. Additionally, the degree of anisotropy is also indicated by the so-called tDA (alternative DA) with values ranging from 1 for perfectly isotropic to infinity for perfectly anisotropic. However, the tDA is not used here in describing the structure according to the invention. Preferably, the geometric degree of anisotropy DA for the artificial trabecular structure of the present invention is in a range of 0.1 to 1.0, in particular 0.2 to 0.8 and more preferably 0.2 to 0.6.

The so-called bone volume/tissue volume fraction (BV/TV) in the cancellous bone area is the unit trabecular volume per total unit volume of a trabecular structure under consideration. An increase in BV/TV can result from a change in various other parameters, e.g. an increase in Tb.Th (FIG. 3B), an increase in Tb.N (FIG. 3C) or a decrease in SMI (FIG. 3D). Preferably, the BV/TV of the trabecular structure according to the invention is in a range of 6% to 70%, and more preferably 20% to 50%.

Finally, the so-called marrow star volume (MSV) defines a respective trabecular porosity of the artificial trabecular structure. More precisely, the MSV determines the size of the hollow spaces in the artificial trabecular structure. The arithmetic mean mMSV according to the invention is preferably in a range of $0.05 \text{ mm}^3$ to $110 \text{ mm}^3$, in particular $0.05 \text{ mm}^3$ to $9 \text{ mm}^3$ and more preferably $0.05 \text{ mm}^3$ to $5 \text{ mm}^3$.

Figure 4:
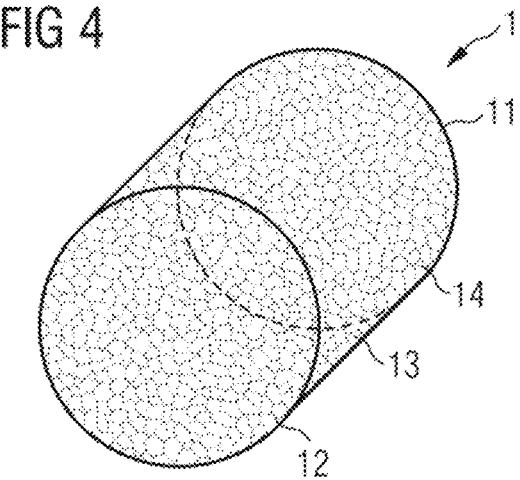
FIG. 4 is a simplified perspective view of a joint implant according to a first example of the invention.

FIG. 4 shows a simplified perspective view of the implant 1 according to a first example of the invention. The implant 1 comprises a rod-shaped body with a macro structuring in the form of a solid cylinder. The implant can be used as joint implant 1 in the bone according to FIG. 1 in such a manner that it is preferably arranged slightly recessed in the bone in the area of the cartilage 2. This allows a cover area 12 of the joint implant 1 to act as a growth area for the tissue or articular cartilage to be newly formed 2. The lower part of the joint implant 1 is preferably located partially or completely in the cancellous bone area 3.

As shown in FIG. 4, the above-described artificial microstructure or trabecular structure 14 can be formed in the entire volume of the implant body. For example, the artificial microstructure or trabecular structure of the joint implant 1 that is open and permeable to bodily fluids allows rapid colonisation of the trabecular surface with cells such as chondroblasts, which results in significantly accelerated overgrowth. Furthermore, depending on its structure and coating, the joint implant 1 according to the invention allows the growth of regenerative fibrous cartilage, or even high-quality hyaline regenerative cartilage, particularly on the cover area 12.

Preferably, the rod-shaped body of the joint implant 1 has a length of at least 0.6 cm and at most 1.2 cm for application in the patella and extremely small joints such as the hand or ankle joints and at least 0.8 cm and at most 2.2 cm, in particular 1.0 cm to 1.6 cm and more preferably 1.25 cm, for proximal and distal tibial and femoral application respectively in the knee and hip joint. This allows optimal accessibility and growing-in of mesenchymal stem cells. The rod-shaped body of the joint implant 1 can further have a diameter of at least 2 mm and at most 6 mm, preferably 3 mm, thus making it possible to achieve an optimal lateral surface facing the synovia for the formation of replacement cartilage tissue.

By means of the individual mesh structure of the artificial microstructure or trabecular structure, that mimics the natural trabecular structure, of the implant 1, one can achieve optimum growth of endogenous tissue into the boundary volume between the joint implant 1 and the indentation or drill channel, in particular into the internal volume of the sleeve area 13 of the joint implant 1 and the end of the joint implant 1 facing the synovia (joint space). Furthermore, the transitions (contact points) of implant 1 on natural bone area are mechanically optimized.

Preferably, the joint implants 1 are configured as microstructured rods based on medically approved, bioinert and biocompatible 3D-printable materials such as for example non-bioresorbable polymers, in particular polyamide (PA), polyether ketones, in particular PEK [polyether ketone], PEKK [poly(ether ketone ketone)], PEEK [polyether ether ketone], polyethylene (PE), in particular UHMWPE [ultra high molecular weight polyethylene], or e.g. bioresorbable polymers, in particular PCL [poly-ε-caprolactone].

Alternatively, metals and metal alloys, preferably those suitable for 3D printing, in particular titanium (pure titanium grade 1), in particular Ti64 (Ti6Al4V), Ti64 ELI and TiCP, stainless steel, in particular 316L, and cobalt-chromium alloys, in particular CoCr, can also be used as materials for the joint implants 1 and in particular for their artificial trabecular structures, including resorbable, 3D-printable biocompatible metal alloys, in particular Mg alloys such as Mg—Ca, Mg—Zr and Mg—Zn of high load-bearing capacity and resorption rate of from 2 mm/year up to 3 mm/year. Said Mg alloys are advantageous because implants with mechanical properties (density (1.8–2.1 gm/cm3) and elastic modulus (30 GPa-45 GPa) similar to those of bone can be produced therefrom.

Furthermore, non-bioresorbable ceramics, preferably suitable for 3D printing, in particular aluminium oxide [$Al_2O_3$], and zircon dioxide [$ZrO_2$] ceramics, or bioresorbable ceramics, in particular calcium phosphate [$Ca_3(PO_4)_2$] ceramic, can also be used as materials for the joint implants 1.

Preferably, $Si_3N_4$ can also be used as a material for the artificial microstructure or trabecular structure of the implant or joint implant 1.

Generally speaking, further medically approved, bioinert and biocompatible materials, in particular suitable for 3D printing, can also be used for the joint implants 1 and in particular for the artificial trabecular structures 14 according to FIGS. 3A to 3F.

Figure 5:
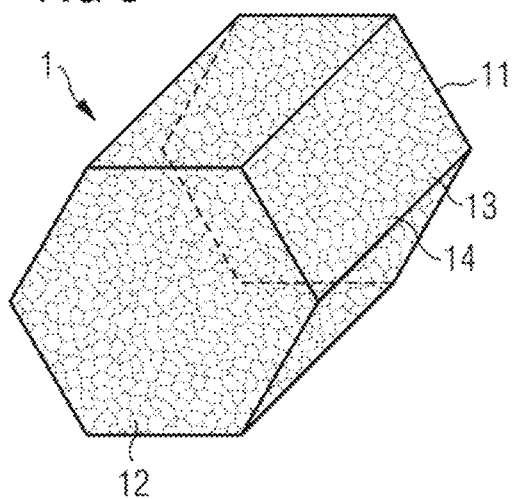
FIG. 5 is a simplified perspective view of a joint implant according to a further example of the invention.

FIG. 5 shows a simplified perspective view of the joint implant 1 according to a further example of the invention, wherein the same reference numbers indicate the same or corresponding elements, and a repeated description thereof will therefore be dispensed with below. According to FIG. 5, the rod-shaped body of the joint implant 1 can also have the form of a prism. Owing to the macrostructuring, for example in the form of a polygonal cross section, what is obtained is a further improved anchoring of the joint implant 1 in the bone or cancellous bone area 3, thus further improving the durability of the joint implants.

Figure 6:
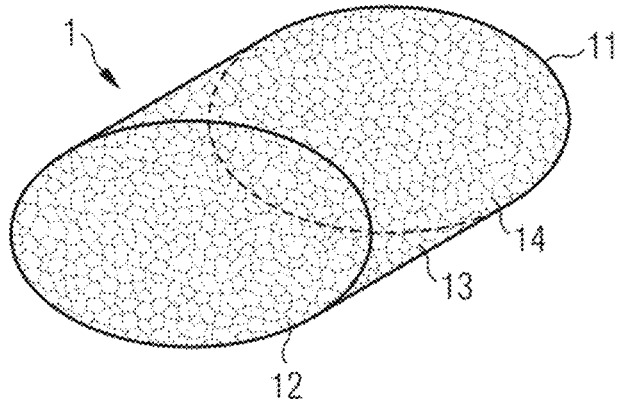
FIG. 6 is a simplified perspective view of a joint implant according to a further example of the invention.

FIG. 6 shows a simplified perspective view of the rod-shaped body of the joint implant 1 according to a further example of the invention, wherein the same reference numbers indicate the same or corresponding elements, and a repeated description thereof will therefore be dispensed with below. Alternatively, according to FIG. 6, it is also possible to use, as macrostructuring, a cross-sectionally elliptical body as joint implant 1, wherein an improved anchoring and in particular a reduced rotatory mobility around the longitudinal axis is again achieved, but the appearance of undesired breakage segments on edges and corners is reduced. Durability is thereby further increased.

Figure 7:
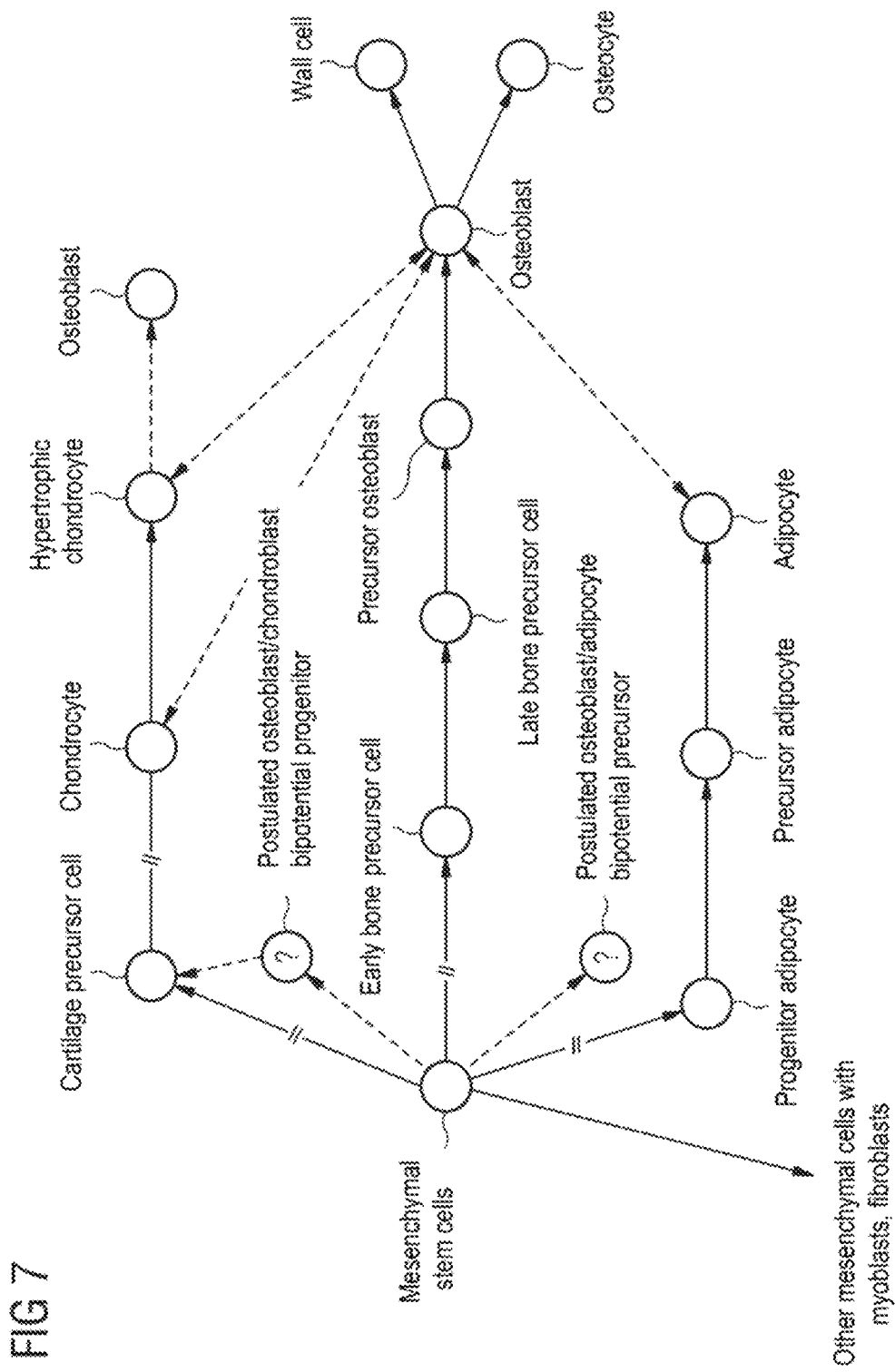
FIG. 7 is a schematic overview of the various differentiation stages of mesenchymal stem cells according to Aubin 1998.

FIG. 7 shows a schematic overview of the various differentiation stages of mesenchymal stem cells according to Aubin 1998. According to the invention, it is desirable for mesenchymal stem cells (MSC) to differentiate into chondrocytes at least in the cover area 12 of the rod-shaped body of the joint implant 1 in order to achieve the new cartilage formation desired in this area. On the other hand, differentiation of the mesenchymal stem cells (MSC) into osteocytes can be advantageous in the lower part or base area 11 of the rod-shaped body of the joint implant 1 in order to facilitate bone formation and thus optimum growth of the joint implant 1 into the cancellous bone area 3.

Surprisingly, it was found that such differentiation of mesenchymal stem cells can already be facilitated by producing a corresponding substrate. More specifically, it was found that a hydrophobic surface of a substrate facilitates chondroblast and in particular chondrocyte differentiation of mesenchymal stem cells and thus cartilage formation, while a hydrophilic surface of a substrate or base facilitates osteoblast differentiation of mesenchymal stem cells and thus bone formation.

The terms "hydrophobicity" or "hydrophobic surface" and "hydrophilicity" or "hydrophilic surface" are defined below based on the so-called contact angle of a water droplet on a surface. Here, hydrophobic surfaces show a contact angle of greater than or equal to 90°, wherein contact angles of greater than 160° characterise superhydrophobic surfaces. The most widely-known representative of these superhydrophobic surfaces is the so-called "lotus plant" has a contact angle of up to 170°. On the other hand, hydrophilic surfaces are characterized by a contact angle of less than 90°.

According to the invention, this differentiation property of the stem cells as a function of the hydrophobicity or hydrophilicity of a surface can be utilized in that the rod-shaped body of the joint implant 1 has corresponding hydrophobic surfaces that facilitate chondrocyte differentiation of the mesenchymal stem cells and thus cartilage formation.

Here, the entire rod-shaped body can have a hydrophobic surface, but it is also possible for only a part of the body to have hydrophobic surfaces. For example, at least the cover area 12 has a hydrophobic surface in order to facilitate cartilage growth at this site. On the other hand, the rod-shaped body can also have a hydrophobic surface in its cover area 12 and upper sleeve area 13, while the base area 11 and the lower part of the sleeve area 13 have a hydrophilic surface. In this manner, cartilage growth can be facilitated in the upper area of the joint implant 1 (the area protruding from the bone) and bone growth can be facilitated in the lower area of the joint implant (the area located in the bone).

According to the invention, a surface that is hydrophobic and thus facilitates chondrocyte differentiation can be implemented in a variety of ways. On the one hand, chemical coatings can be applied to the rod-shaped body, and in particular its artificial trabecular structures, which improves hydrophobic (water-repelling) properties.

Figure 8A:
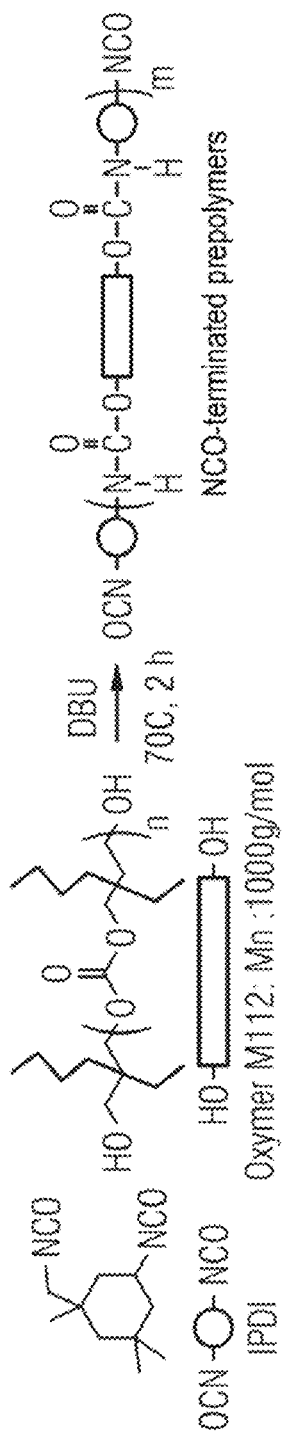
FIGS. 8A and 8B illustrate the production of a hydrophobic chemical coating using the example of segmented polyurethanes.
Figure 8B:
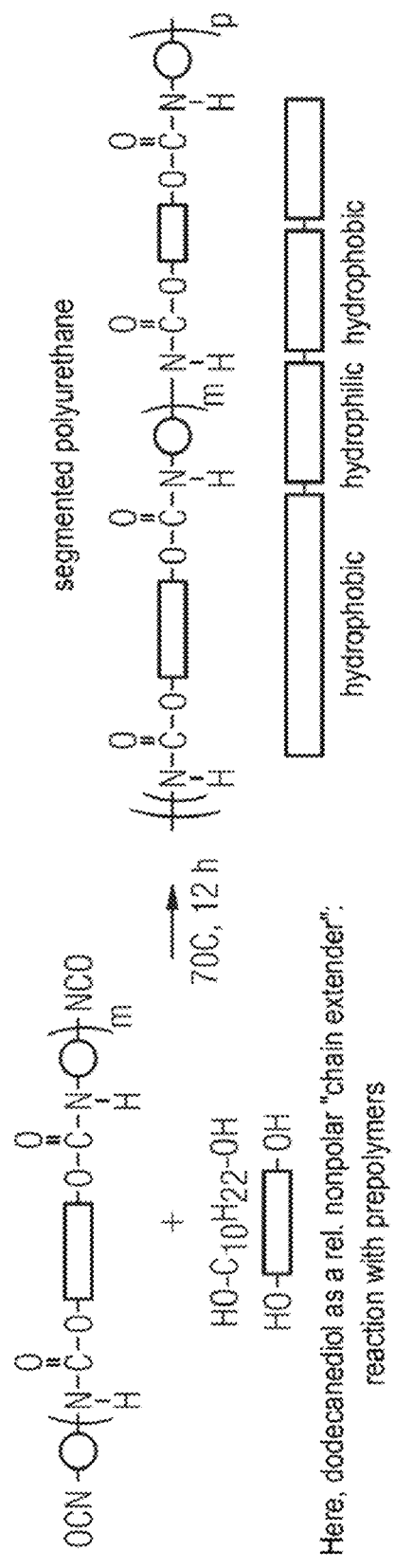

FIGS. 8A and 8B illustrate the production of such a hydrophobic coating using the example of segmented polyurethanes such as those that can be applied to an artificial microstructure or artificial trabecular structure of the joint implant 1 according to the invention.

According to FIG. 8A, the production of NCO-terminated prepolymers is first illustrated, wherein there is a stoichiometric excess of —NCO. According to FIG. 8B, the NCO-terminated prepolymers are then converted using dodecane diol as a non-polar "chain extender" into the desired segmented polyurethane (segmented PU).

Figure 9A:
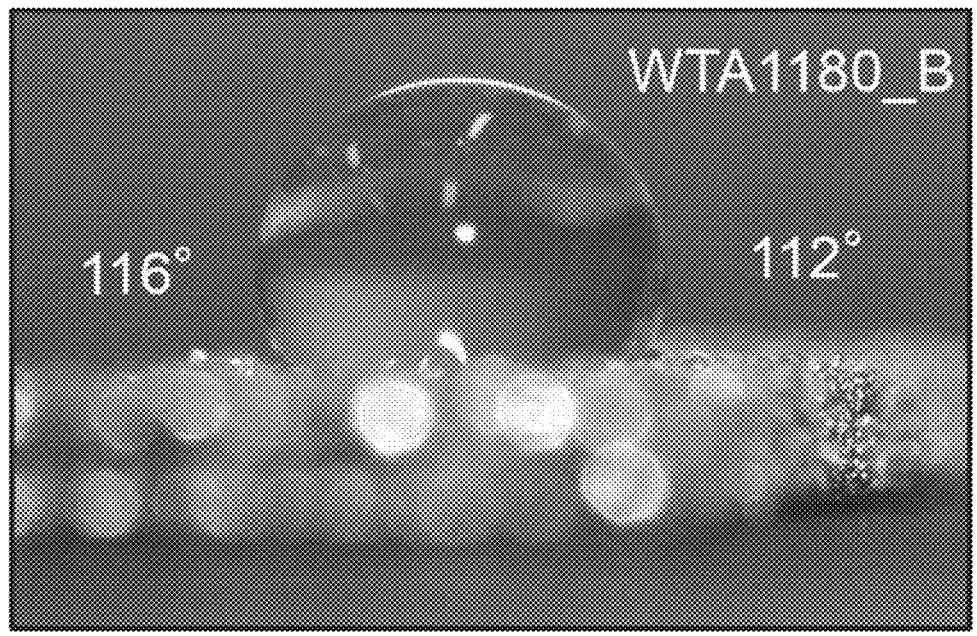
FIGS. 9A and 9B are enlarged views of Ti substrates coated with segmented PU in order to illustrate respective contact angles.

FIG. 9A shows an enlarged view of a Ti substrate coated with such a segmented PU. While an uncoated Ti substrate (not shown) has a contact angle of 0°, the Ti surface coated with segmented PU (10% PU in toluene) has contact angle of approx. 112° to 116°.

Figure 9B:
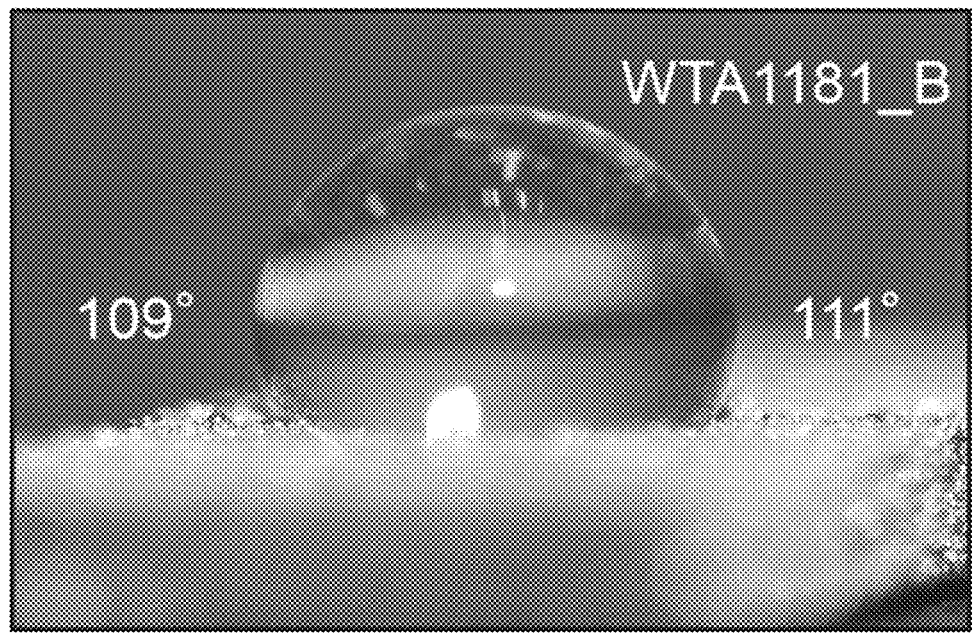

FIG. 9B shows an enlarged view of a Ti substrate coated with a segmented PU, wherein the concentration of the segmented PU is 2% in toluene. The Ti surface coated with such segmented PU now has a contact angle of approx. 109° to 111°.

The following components were used for the above-described hydrophobic PU coating:
a) aliphatic diisocyanates: isophorone diisocyanate (IPDI), hexamethylene diisocyanate (HDI) and dicyclohexyl-methane diisocyanate (hydrogenated MDI, HMDI)
b) polyols: polycarbonate diols (hydrolysis resistance) such as e.g. Desmophen C2200, Desmophen XP2586, and hydrocarbon diols based on natural rubber and hydrogenated natural rubber
c) chain extenders: aliphatic diols such as hexanediol, decanediol and possibly longer diols because of their hydrophobicity Furthermore, a PU-based polyelectrolyte complex can also be used as a hydrophobic chemical coating. Here, the same components as mentioned above are used, wherein sulfonated diols or ammonium-group-containing diols are additionally used as chain extenders in order to introduce ionic groups for forming the electrolyte complexes.

Complex formation then takes place after coating (preferably dip coating) by immersion in a dilute solution with a surfactant (cationic or anionic, depending on which ionic groups are present in the polymer). The ionic interactions between the polyelectrolytes and the surfactant lead to a solid bond, particularly when the surfactant is hydrophobic and thus already has no tendency to dissolve in an aqueous environment.

Furthermore, an acrylate-based polyelectrolyte complex can also be used as a hydrophobic chemical coating, wherein a first layer of polyelectrolytes such as polyacrylic acid or copolymers containing acrylic or methacrylic acid, optionally also with their own phosphoric acid groups (comonomer vinylphosphonic acid) is applied to the surface for adhesion and a second layer is then applied as described above (a coating of a surfactant solution, coordinated with the ionic groups of the polyelectrolyte).

Preferably, the following three types of hydrophobic coating materials are used:
crosslinked polyurethane
uncrosslinked polyurethane and
polyelectrolyte complexes
which have the following characteristics:

Crosslinked Polyurethane:
Polyurethanes differ from most other polymers and plastics in that they are composed of a "modular system" of many different components (diisocyanates, polyisocyanates, polyols, chain extenders, soft segments etc.). The actual construction thereof (chemical synthesis of the polymer molecules) typically occurs only during processing, so that the user or manufacturer of components based on polyurethanes can assemble the final properties in a manner tailored to his requirements. Almost all other plastics, in contrast, are produced and supplied with fixed property profiles by the raw material manufacturer (chemical industry), so that the user or producer of components has only a relatively minimal influence on their property profile. For this reason, polyurethanes constitute a highly favourable starting point for special developments such as the coating of the implant body according to the invention 1.

Polyurethanes have long been used as biocompatible active compounds, for example as inert, non-degradable coatings for cardiac pacemakers, or also as biocompatible, degradable carrier materials (scaffolds) for tissue engineering or regenerative medicine. In such use, the properties thereof (e.g. hydrophobicity/hydrophilicity, degradability/long-term stability, strength, stiffness, porosity etc.) are adjusted by combining the components as required.

Crosslinked polyurethanes are produced in a dilute solution in the presence of the substrate to be coated. In this process, the components can be selected in such a way that chemical bonding to the surface of the substrate to be coated also takes place simultaneously during cross-linking. These materials often show outstanding adhesion without requiring adhesion promoters or similar intermediate layers, particularly to hydrophilic surfaces. The components of the polyurethanes can be selected such that the layers produced are themselves hydrophobic.

Suitable components are aliphatic di- and polyisocyanates for biocompatibility, soft segments and polycarbonate-, silicone- or polybutadiene-based polyols for long-term stability, and long-chain diols, possibly also silicone- or polybutadiene-based, as chain extenders for hydrophobicity.

The main drawback is the problematic control of the layer thickness during coating. The concentration is the only independent parameter that can be varied to influence the layer thickness. Although the composition and the reaction time affect the layer thickness, the composition also affects all of the other properties, and the reaction time cannot be set to any desired duration, because complete reaction of the isocyanate groups is necessary for biocompatibility, so the coating time cannot be reduced to any desired duration.

Uncrosslinked Polyurethanes:
Uncrosslinked polyurethanes are produced separately from the coating process and then transferred from a dilute solution to an immersion process. The setting of properties offers the same possibilities as in the case of the crosslinked polyurethanes, as almost all of the components can be used in both cases.

The advantage of the uncrosslinked polyurethanes is that synthesis and coating take place separately from each other, so that there are better possibilities for controlling the layer thickness. The concentration, the exposure time during the immersion process, and above all the number of immersions (with respective drying steps between them) determine the thickness of the applied layer.

The drawback of this is that chemical bonding of the layer of the substrate requires either an adhesion promoter layer or special components in the polyurethane that can react with the surface. In some cases, the adhesion of these layers is thus less long-lasting, or the coating process is more expensive, because an adhesion promoter layer must be added before the actual coating is carried out. However, as this is presumably also possible as a simple immersion coating, the additional expense is limited.

Polyelectrolyte Complexes:

Polyelectrolyte complexes utilize electrostatic interactions between positively and negatively charged ions and surfaces. Each material has a specified surface charge in water (its zeta potential), which—depending on the chemical structure—is either positive or negative. Neutral particles or surfaces also possess this surface charge. Polyelectrolytes having charges along the polymer chain that are opposite to this surface charge adhere very strongly to the surface. In general, they can no longer be removed, because each polymer chain, depending on its chain length, adheres simultaneously with dozens or hundreds of groups and is therefore maintained in position even if some of these groups are dissolved due to external influences. As one possibility, oppositely charged polyelectrolytes can then be deposited on these polyelectrolytes, thus making it possible to precisely set the layer thickness on a molecular basis by alternating deposition (layer by layer technology). Alternatively, low-molecular-weight ions, e.g. surfactants or soaps, are deposited, one end of which carries a charge opposite to that of the polyelectrolyte in order to ensure adhesion, and the other end of which is hydrophobic. In the ideal case, layers can be produced in this manner that show a thick layer of e.g. methyl groups toward the outside, thus making it possible to achieve surface tension that is almost identical to that of fluoropolymers (PTFE, Teflon).

The advantages of these materials lie in their ordinarily outstanding adhesion in aqueous or non-aqueous systems, in the precise controllability of the layer thickness, and in their relatively easy-to-control, highly pronounced hydrophobicity.

A drawback is the deposition in almost monomolecular layers, which in the case of larger layer thicknesses requires a large number of immersions in alternating polyelectrolyte baths. However, as drying steps are not required between these immersions, the expense is acceptable.

Furthermore, as a starting material for the rod-shaped body of the joint implant 1, 3D-printable materials can be used that already show a hydrophobic surface per se (e.g. without additional micro- and/or nanostructuring and/or chemical coating). For example, the untreated surface of a zircon dioxide ceramic substrate already has hydrophobic properties.

Moreover, the artificial microstructures or trabecular structures 14 can comprise an additional growth coating or a growth factor in order to improve cartilage differentiation and the growth of cartilage material. Preferably, the artificial trabecular structure 14 can be coated with specific human and human homologous growth factors, FGFs [fibroblast growth factors], in particular FGF-1, FGF-2 and FGF-10 to FGF-22 and in particular FGF-18. Alternatively, the artificial trabecular structure 14 can be coated with specific human and human homologous growth factors, SDFs [stromal cell-derived factors], in particular SDF-1. Furthermore, specific human and human homologous growth factor, IGF-1 [insulin-like growth factor 1], human PDGF [platelet-derived growth factor], the specific human and human homologous growth factors TGF-β1 and TGF-β3 [transforming growth factors beta 1 and beta 3] or specific human and human homologous BMP-2 and BMP-7 [bone morphogenetic protein-2 and protein-7] can be applied to the artificial trabecular structure 14. Further possibilities for the coating include specific human and human-homologous OP-1 [osteogenic protein-1], human PRP [platelet-rich plasma] and bioinert polyamides especially suitable for coatings. Of course, combinations of the above-described coatings are also possible. Preferably, the growth factor can be applied as the last layer.

According to the invention, by correspondingly selecting suitable bioinert and biocompatible materials with ideal adaptation of the geometric and chemical/biochemical surface structure (artificial trabecular structure), the differentiation of mesenchymal stem cells into chondroblasts or osteoblasts can be selectively controlled. This allows the cartilage structure on the side of the joint implants 1 facing the synovia in particular (cover area 12) to be improved by means of the above-described hydrophobic coatings and the growth factors that stimulate cartilage formation. Moreover, on the side of the joint implants facing away from the synovia (base area 11), bone formation and bone structure in the cancellous bone area can be improved by means of hydrophilic surface structures and coatings. In this manner, one achieves almost physiological suitability, as the joint anatomy and natural bone stability are not or only minimally affected such as e.g. in the case of implantation of an endoprosthesis. The compatibility and efficacy of the curative therapy is thus significantly improved by means of the above-described joint implants.

The combination of the above-described biocompatible, bioinert, 3D-printable materials, the specifically suitable biomedical geometries (curvature, nanostructure, microstructure and macrostructure) and the growth-promoting coatings provides a novel joint implant that can further optimize the quantity and quality and thus the load-bearing capacity and durability of replacement cartilage tissue and make a substantial contribution to the curative treatment of joint diseases (arthrosis).

Figure 10:
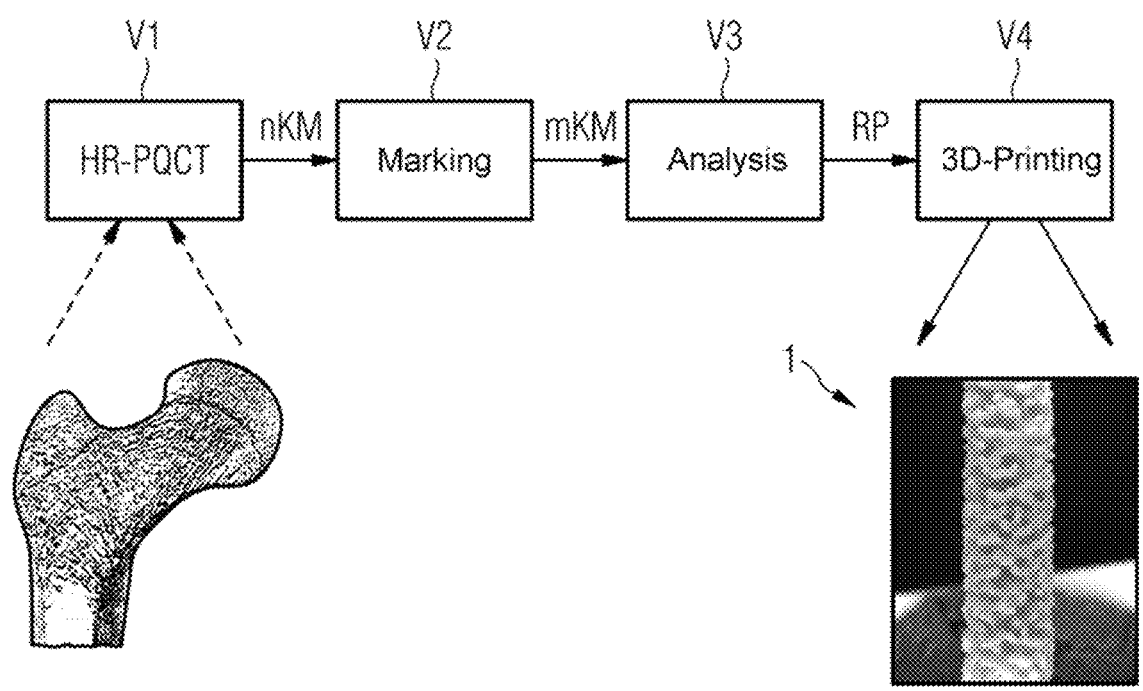
FIG. 10 shows a simplified block diagram of a device for producing an implant according to an example of the invention.

FIG. 10 shows a simplified block diagram of a device for producing an implant 1 according to a preferred example of the invention.

According to FIG. 10, a capture device V1 captures a natural bone microstructure of a natural bone area, such as e.g. the part of a femoral bone as depicted in FIG. 1. For example, the capture device V1 can comprise a high-resolution peripheral quantitative computed tomograph (HR-pQCT). Alternatively, it is however also possible to use other imaging devices which allow a sufficiently accurate three-dimensional reproduction of a particular bone microstructure.

For example, the capture device V1 generates a multiplicity of two-dimensional (2D) sectional views in the bone area to be examined. The capture device XtremeCT®, as used in experiments, has e.g. a resolution of 82 μm, thus yielding for 110 sectional views a depth of 9.02 mm of the bone area examined, which is sufficient for the present joint implant.

Figure 11:
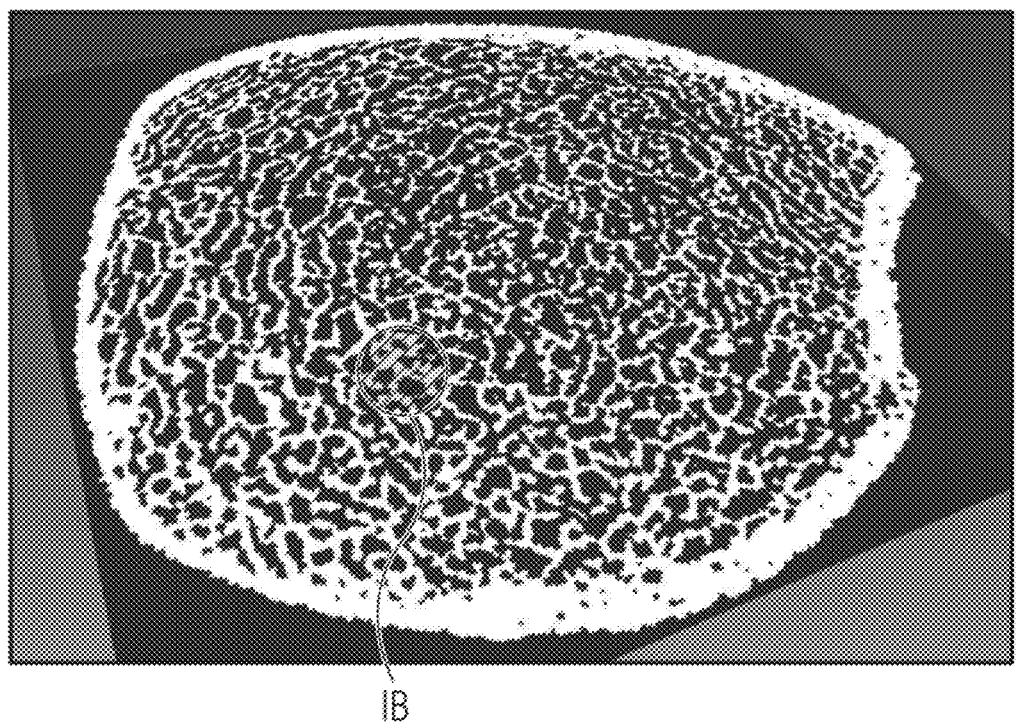
FIG. 11 shows a simplified top view of a 2D sectional view in a bone area to be examined.

FIG. 11 shows a simplification of such a 2D sectional view in a bone area to be examined.

By means of the marking device V2 as depicted in FIG. 10, it is then possible for a user (e.g. attending physician) to define an implant area IB. What are selected and marked here are essentially a scanning orientation (direction in which the sectional views are generated), a length (number of sectional view+resolution (or interval of the sectional views)) and also a two-dimensional macrostructure (circle, polygon, ellipse) for a predetermined bone area.

Figure 12A:
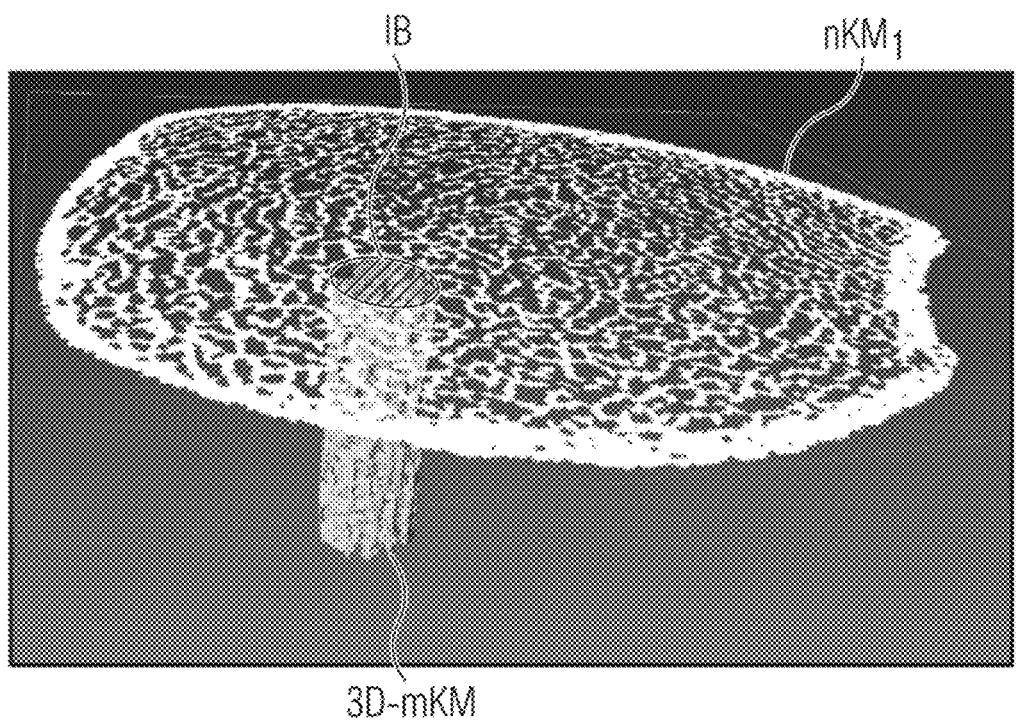
FIGS. 12A to 12C show simplified perspective illustrations of 2D sectional views and of a resultant three-dimensional marked natural bone microstructure in a bone area to be examined.
Figure 12B:
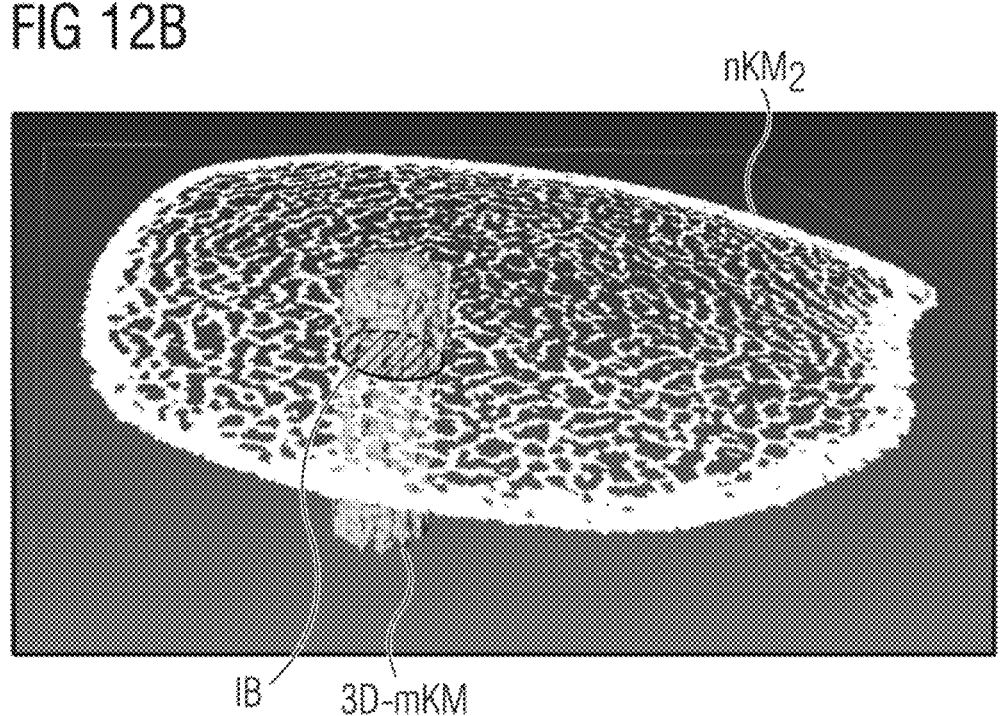
Figure 12C:
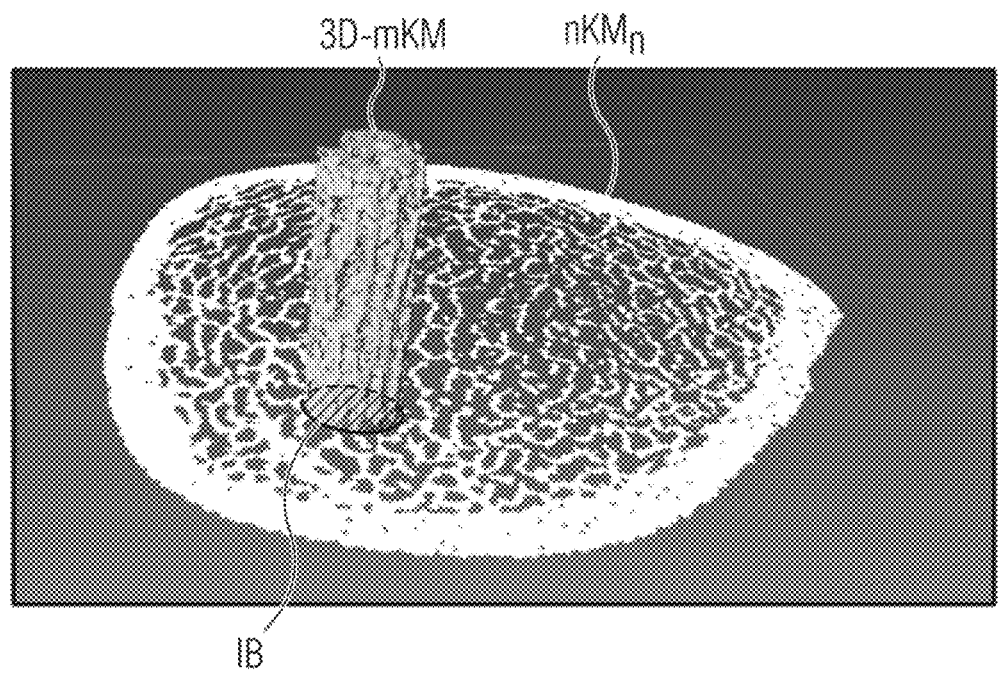

As depicted in a simplified manner in FIGS. 12A to 12C, what is obtained on the basis of the multiplicity of two-dimensional sectional views $nKM_1$ to $nKM_n$ of the natural bone microstructure nKM and of the marking of the envisaged implant area IB as carried out by means of the marking device V2 is an exact image 3D-mKM of the marked natural bone microstructure for the desired implant or the captured bone microstructure for the marked implant area IB.

By means of the analysis device V3 as depicted in FIG. 10, it is further possible to carry out an analysis of said image 3D-mKM or of the captured bone microstructure in the marked implant area IB to ascertain reproduction parameters RP.

For example, it is possible to ascertain a multiplicity of disc parameters, which are essentially based on the data of the two-dimensional sectional views and a thickness of the discs, for example resolution of the capture device V1. In this case, the analysis device V3 simplifies each captured two-dimensional sectional view $nKM_1$ to $nKM_n$ to give a disc having a predetermined thickness (e.g. resolution), the two-dimensional structure being identical for the entire disc thickness (i.e. from top to bottom).

Alternatively, the captured bone microstructure 3D-mKM in the marked implant area or the multiplicity of captured two-dimensional sectional views $nKM_1$ to $nKM_n$ can also be converted into a multiplicity of trabecular parameters as reproduction parameters. In contrast to the above-described disc parameters, which generate a gradation from disc to disc, what is carried out here is essentially a linearization for the non-captured gaps between the captured two-dimensional sectional views $nKM_1$ to $nKM_n$ in order to generate the trabecular parameters as reproduction parameters RP. Such an analysis method can further improve the accuracy in the reproduction of the natural bone microstructure. Furthermore, it is possible as a result to considerably reduce a quantity of data or a data transfer-relevant data rate, since the trabecular parameters are essentially vector data.

Lastly, what is carried out in the reproduction device V4 according to FIG. 10 is construction of an artificial microstructure or trabecular structure 14 on the basis of the ascertained reproduction parameters and for the production of the desired implant I. For example, the reproduction device V4 can comprise a 3D printer, thus allowing patient-specific individualization of particular implants in a cost-effective manner.

The structure of the artificial microstructure or trabecular structure 14 of the implant I is thus very similar or virtually identical to the marked natural bone area of a particular patient, thus yielding individually optimal properties for natural healing and for mechanical matching of the implant 1 with the natural bone microstructure (bone continuity) of a particular patient.

Use of disc parameters as reproduction parameters consequently yields an artificial stacked-disc structure for the artificial microstructure of the implant 1. On the other hand, use of trabecular parameters as reproduction parameters yields an artificial trabecular structure for the artificial microstructure 14 of the implant.

Furthermore, it is possible to provide at least one transmission device (not depicted) for sending/receiving the captured natural bone microstructure nKM, the marked natural bone microstructure mKM and/or the ascertained reproduction parameters RP, thus making it possible to produce individual implants in a particularly efficient and cost-effective manner. The transmission device can transmit the data, for example, via secure channels in the Internet, especially to central analysis centres and/or reproduction centres.

FIG. 13 shows a simplified flow chart of a method for producing an implant according to a further example of the invention.

According to FIG. 13, what is carried out after a start in step S0 is, first of all, capture of a natural bone microstructure, for example by generating a multiplicity of sectional views $nKM_1$ to $nKM_n$. In a step S2, what is then carried out is marking of an implant area IB in the natural bone area to generate a marked natural bone microstructure mKM (macrostructure). Furthermore, what is carried out in a step S3 is analysis of the marked natural bone microstructure mKM or of the captured bone microstructure in the marked implant area IB in order to ascertain the reproduction parameters RP. Lastly, what is carried out on the basis of the ascertained reproduction parameters RP in a step S4 is construction of an artificial microstructure to produce the implant 1. The method ends with step S5.

FIG. 13 consequently shows a flow chart for a method and a computer program product according to the present invention. It should be pointed out that each block or step of the flow chart and particular combinations of blocks in the flow chart can be implemented by computer program commands. Said computer program commands can be loaded onto a computer or some other programmable instrument in order to generate a device, wherein the commands executed in the computer or some other programmable instrument generate means for implementing the operation modes, as are depicted in the steps of the flow chart. Said computer program commands can also be stored in a digital storage medium, such as a suitable centralized (cloud) or decentralized mass storage system such as e.g. a CD/DVD, external hard drive or USB, which instructs a computer or some other programmable instrument to realize a certain functionality. Furthermore, the computer program commands or the program code can be downloaded in, for example, a telecommunications network in order to bring about operating steps which are executed on a computer or some other programmable instrument in order to generate a computer-implemented process which makes it possible to carry out the method steps according to FIG. 13.

The invention therefore further encompasses a digital storage medium with electronically readable control signals which can interact with a computer system such that they can execute the method steps according to FIG. 13. Furthermore, the invention relates to a computer program product with program code stored on a machine-readable medium for carrying out the method steps according to FIG. 13, when the program runs on a computer. Apart from that, the present invention relates to a computer program with program code for carrying out method steps according to FIG. 13, when the program runs on a computer.

The invention was described above by means of preferred examples. However, it is not limited thereto, and in particular also comprises individual combinations of the above-described examples. In particular, the preliminary stage of chondrocyte differentiation of mesenchymal stem cells, namely chondroblast differentiation of mesenchymal stem cells, can also be facilitated by the hydrophobic surface. Although the invention has been described above in the context of use in human hip and knee joints, it is not limited to this application and in particular also includes small and extremely small human joints (e.g. foot and finger joints) and animal joints.

LIST OF REFERENCE NUMBERS

1 Implant
2 Articular cartilage
3 Cancellous bone area
4 Periosteum
5 Cortical bone
6 Medullary cavity 7, 8 Trabeculae
11 Floor area
12 Cover area
13 Sleeve area
14 Artificial microstructure
V1 Capture device
V2 Marking device
V3 Analysis device
V4 Reproduction device
IB Implant area
$nKM_x$ Natural bone microstructure
mKM, 3D-mKM Marked bone microstructure
RP Reproduction parameters
S0 to S5 Method steps

The invention claimed is:

1. A method for producing an implant, comprising:
    a) capturing (S1) a natural bone microstructure (nKM) of a natural bone area;
    b) marking (S2) an implant area (TB) in the natural bone area;
    c) analyzing (S3) the captured bone microstructure (3D-mKM) in the marked implant area to ascertain reproduction parameters; and
    d) constructing (S4) an artificial microstructure (14) on a basis of ascertained reproduction parameters to produce the implant (1), wherein
    the implant is a rod-shaped joint implant for new tissue formation at a joint, which has a hydrophobic surface that facilitates chondrocyte differentiation of mesenchymal stem cells.

2. The method according to claim 1, wherein a multiplicity of 2D sectional views ($nKM_1$ to $nKM_n$) is generated by a high-resolution peripheral quantitative computed tomography method (HR-pQCT) when capturing the natural bone microstructure.

3. The method according to claim 1, wherein a multiplicity of disc parameters or a multiplicity of trabecular parameters are ascertained as reproduction parameters (RP) when analyzing.

4. The method according to claim 1, wherein constructing the artificial microstructure (14) is realized using a 3D printing method.

5. The method according to claim 1, wherein artificial microstructure (14) is an artificial stacked-disc structure or an artificial trabecular structure.

6. The method according to claim 1, wherein a material used in the production of the implant is a polymer, a metal, a metal alloy, a magnesium alloy, a ceramic, or $Si_3N_4$.

7. The method according to claim 1, further comprising:
    e) coating artificial microstructure (14) with a hydrophobic chemical material.

8. The method according to claim 7, wherein the hydrophobic chemical material comprises a segmented polyurethane or polyelectrolyte or a hydrophobically functionalized chitosan or chitosan derivative.

9. The method according to claim 1, further comprising:
    e) applying a growth factor to artificial microstructure (14) to facilitate the chondrocyte differentiation of the mesenchymal stem cells.

10. A digital storage medium with electronically readable control signals which can interact with a computer system such that the method according to claim 1 is executed.

11. A computer program product with program code stored on a machine-readable medium for carrying out the method according to claim 1, when the program runs on a computer.

12. A computer program with program code for carrying out the method according to claim 1, when the program runs on a computer.

13. The method according to claim 1, wherein a material used in the production of the implant is a polymer selected from the group consisting of PA, PEK, PEKK, PEEK, UHMWPE, and PCL; a metal selected from the group consisting of Ti and stainless steel; a metal alloy selected from the group consisting of Ti64 and CoCr; a magnesium alloy selected from the group consisting of Mg—Ca, Mg—Zr, and Mg—Zn; ceramic selected from the group consisting of $Al_2O_3$, $ZrO_2$, and $Ca_3(PO_4)_2$, or $Si_3N_4$.

14. A device to produce an implant, comprising:
    a capture device (V1) to capture a natural bone microstructure (nKM) of a natural bone area;
    a marking device (V2) to mark an implant area (TB) in the natural bone area;
    an analysis device (V3) to analyse the natural bone microstructure (mKM) captured in the marked implant area and to ascertain reproduction parameters (RP); and
    a reproduction device (V4) to construct an artificial microstructure (14) on a basis of ascertained reproduction parameters (RP) and to produce the implant (1), wherein
    the implant is a rod-shaped joint implant for new tissue formation at a joint, which has a hydrophobic surface that facilitates chondrocyte differentiation of mesenchymal stem cells.

15. A device according to claim 14, further comprising:
    at least one transmission device for sending/receiving the captured bone microstructure (nKM), the marked bone microstructure (mKM) and/or ascertained reproduction parameters (RP).

16. A device according to claim 14, wherein the capture device (V1) comprises a high-resolution peripheral quantitative computed tomograph (HR-pQCT).

17. A device according to claim 14, wherein the reproduction device (V4) comprises a 3D printer.

18. A method for producing an implant, comprising:
    a) capturing (S1) a natural bone microstructure (nKM) of a natural bone area;
    b) marking (S2) an implant area (TB) in the natural bone area;
    c) analyzing (S3) the captured bone microstructure (3D-mKM) in the marked implant area to ascertain reproduction parameters;
    d) constructing (S4) an artificial microstructure (14) on a basis of ascertained reproduction parameters to produce the implant (1); and
    e) coating artificial microstructure with a hydrophobic chemical material.

19. A method for producing an implant, comprising:
    a) capturing (S1) a natural bone microstructure (nKM) of a natural bone area;
    b) marking (S2) an implant area (TB) in the natural bone area;
    c) analyzing (S3) the captured bone microstructure (3D-mKM) in the marked implant area to ascertain reproduction parameters;
    d) constructing (S4) an artificial microstructure (14) on a basis of ascertained reproduction parameters to produce the implant (1): and
    e) coating artificial microstructure with a hydrophobic chemical material, wherein the hydrophobic chemical material includes a segmented polyurethane or polyelectrolyte or a hydrophobically functionalized chitosan or chitosan derivative.

* * * * *